United States Patent [19]
Rodriguez et al.

[11] Patent Number: 5,788,985
[45] Date of Patent: Aug. 4, 1998

[54] VACCINE COMPOSITION FOR ELICITING AN IMMUNE RESPONSE AGAINST N-GLYCOLYLATED GANGLIOSIDES AND ITS USE FOR CANCER TREATMENT

[75] Inventors: Rolando Pérez Rodriguez; Luis Enrique Fernandéz Molina; Gilda Marquina Rodriguéz; Adriana Carr Pérez; Oscar Gonzalo Valiente Hernandéz, all of Habana, Cuba

[73] Assignee: Centro de Inmunologia Molecular, Habana, Cuba

[21] Appl. No.: 365,684

[22] Filed: Dec. 29, 1994

[30] Foreign Application Priority Data

Dec. 29, 1993 [CU] Cuba .......................... 131/93

[51] Int. Cl.$^6$ .......................... A61K 39/00; A61K 45/00
[52] U.S. Cl. .......................... 424/277.1; 424/184.1;
424/277.1; 424/137.1; 424/422; 424/423;
424/283.1; 424/278.1; 424/194.1; 424/234.1;
424/141.1; 424/155.1; 424/156.1; 424/174.1;
530/387.5; 530/389.7; 530/395; 530/806;
530/828; 530/387.7; 530/388.1; 514/42;
514/25; 514/885
[58] Field of Search .......................... 424/184.1, 277.1,
424/137.1, 422, 423, 283.1, 278.1, 194.1,
234.1, 141.1, 155.1, 156.1, 174.1; 436/813,
822, 823; 514/42, 25, 885; 530/387.5, 389.7,
395, 806, 828, 387.7, 388.1

[56] References Cited

U.S. PATENT DOCUMENTS 5,026,557 6/1991 Estis et al. .
5,102,663 4/1992 Livingston et al. .

FOREIGN PATENT DOCUMENTS 0280209 8/1988 European Pat. Off. .
0586002 3/1994 European Pat. Off. .
8706840 11/1987 WIPO .
9014104 11/1990 WIPO .

OTHER PUBLICATIONS

Furukawa et. al. (1988) J. Biol. Chem. vol. 263 (34), 18507-18512 Analysis of the Expression of N-Glycolylneuraminic Acid.

Dohi et. al. (1988) Cancer. Res. vol. 48, 5680-5685 An IgG$_3$ Monoclonal Antibody Established After Immunization.
Hamilton et. al. (1993) Int. J. Cancer vol. 53, 566-573 Gangliosid Expression on Human Malignant Melanoma.
Portoukalian et. al. (1991) Int. J. Cancer. vol. 49, 893-899 Humoral Immune Response in Disease-Free Advanced Melanoma.
Article entitled: $G_{M2}$-KLH Conjugate Vaccine: Increased Immunogenicity in Melanoma Patients After Administration With Immunological Adjuvant QS-21. Authors: Friedhelm Helling, Shengle Zhang, Ann Shang, Sucharita Adluri, Michele Calves, Rao Koganty, B. Michael Longenecker, Tzy-J. Yao, Herbert F. Oettgen, and Philip O. Livingston—Published in Cancer Research 55. 2783-2788, Jul. 1, 1995.
Article entitled: GD3/Proteosome Vaccines Induce Consistent IgM Antibodies against the Ganglioside GD3. Authors: Philip O. Livingston, Michele J. Calves, Friedhelm Helling, Wendell D. Zollinger, Milan S. Blake and George H. Lowell—Published in Vaccine. vol. 11, Issue 12, 1993.
Article entitled: Characterization of IgG and IgM Antibodies Induced in Melanoma Patients by Immunization with Purified $G_{M2}$ Ganglioside. Authors: Philip O. Livingston, Gerd Ritter, Pramod Srivastava, Maureen Padavan, Michele J. Calves, Herbert F. Oettgen and Lloyd J. Old—Published in Cancer Research 49, 7045-7050, Dec. 15, 1989.
Article entitled: Humoral Immune Response in Disease-Free Advanced Melanoma Patients After Vaccination with Melanoma-Associated Gangliosides. Authors: Jacques Portoukalian, Stefan Carrel, Jean-Francois Dore and Philip Rumke, on behalf of the EORTC Cooperative Melanoma Group—Published in the International Journal of Cancer 49, 893-899 (1991).

Primary Examiner—Paula K. Hutzell
Assistant Examiner—Khalid Masood
Attorney, Agent, or Firm—Trask, Britt & Rossa

[57] ABSTRACT

The invention provides novel uses for n-glycolylated gangliosides, or derivatives and/or oligosaccharides thereof. The invention further provides methods of obtaining such gangliosides, as well as vaccine compositions comprising said gangliosides. The gangliosides may be coupled to carriers and may be accompanied by adjuvants. The vaccine compositions can be used in the treatment of breast cancers, whereby the gangliosides are used to elicit an immune response to corresponding gangliosides on breast tumour cells.

18 Claims, No Drawings

VACCINE COMPOSITION FOR ELICITING AN IMMUNE RESPONSE AGAINST N-GLYCOLYLATED GANGLIOSIDES AND ITS USE FOR CANCER TREATMENT

FIELD OF THE INVENTION

The present invention relates to the field of active specific immunotherapy of cancer and among other things provides a vaccine composition for producing or increasing the antibody immune response against N-glycolylated gangliosides, especially N-glycolyl GM3 (NGcGM3), which can be used for the prevention and treatment of cancer.

DESCRIPTION OF THE PRIOR ART

Gangliosides are glycosphingolipids that contain sialic acid and are expressed in all mammalian cell membranes. They comprise a saccharidic polar part and a hydrophobic ceramide (sphingosine and a long chain fatty acid).

These compounds insert in the lipid bi-layer that forms the external cell membrane leaving the oligosaccharide chain exposed to the external surroundings.

Ganglioside expression varies in the different cell differentiation stages and growth fashions. The differentiation or dedifferentiation that occurs during oncogenic transformation is associated with changes that occur in the distribution of the gangliosides.

Moreover, the expression of certain gangliosides in mammalian tissues is species restricted. These gangliosides (called heterophiles) contain N glycolyl neuraminic acid and are present in most species (mice, rats, dogs, horses, pigs, etc.) except humans and chickens.

This "non self" characteristic of the N-glycolylated gangliosides has a very important incidence in the immunogenicity of these compounds in humans. This fact was indirectly observed in the 20's by Hanganatziu and Deicher (H-D), a time when treatment of certain diseases with horse serum was common practice.

These patients developed a disease called "serum sickness". It was shown that their serum reacted with components of the horse antiserum as well as erythrocytes of different species.

Later these H-D antigens were extracted as horse erythrocyte gangliosides and their main epitope defined as NGcNAα(2→3)Galβ(1→4)Glc (1→R).

Experiments performed with cultured human tumour cells and H-D antiserum demonstrated the presence of these antigens in a group of human tumours. Thus, a tumour specific antigen seemed to have been found.

Later cell culture experiments using bovine serum free medium and the determination of the presence of lipid bound NGcNA in ganglioside extracts of tumour biopsies done by Gas Chromatography Mass Spectrometry techniques showed that the level of N-glycolylated gangliosides in the tumours studied was below 0.05% of the total sialic acid (Furukawa et al (1988) J. Biol. Chem. 263, 18507).

Based on these results, the consensus has become that the N-glycolylated gangliosides have no practical value as targets for cancer immunotherapy.

Nevertheless in the present invention it is shown that breast cancer seems to be an exception. N-glycolylated gangliosides are present in relatively large amounts (Patent application (Cuba) No. 131/93).

Tumour associated gangliosides have been used as targets in treatment approaches, mainly in neuroectodermic derived tumours (Gangliosides and Cancer Ed. H. F. Oettgen (1989) p.7).

These approaches are based, in general, on two principles: passive immunotherapy with specific mAbs and active immunization with the referred gangliosides.

Immunization protocols with GM2 ganglioside absorbed to BCG have been performed in patients with melanoma. The presence of anti-GM2 antibodies of IgM and IgG isotypes was determined in these patients. Patients with higher titers showed a more delayed relapse of 15 months (Livingston et al (1989), Cancer Res. 49, 7045–7050).

Moreover, preliminary clinical trials in patients with melanoma have been performed. Immunizations with mixtures of gangliosides, obtained from primary tumour cells, alone or included in liposomes showed low antibody titers, mainly of IgG isotype, against gangliosides GM3, GD3, GM2 and 9-0-Acetyl GD3.

This antibody response was short lasting and could not be maintained or increased by repetitive immunizations. Nevertheless, the patients with immune response showed once more a statistically significant delayed relapse (Portoukalain et al (1991), Int. J. Cancer 49, 893–899).

To improve the immune response against gangliosides, clinical trials of melanoma patients using protein-GM2 ganglioside conjugates, particularly KLH-GM2, have started.

Results obtained until now indicate a higher production of IgM antibody titers and the presence of specific IgG antibodies with effector qualities, although the immune response is not a typical T cell dependent antigen secondary response (Livingston (1993) Proceedings of the Conference "Specific Immunotherapy of Cancer with Vaccines". The N.Y. Academy of Science; abst. 24).

Recent experiments on the immunogenicity in mice using GD3 coupled to other vehicles, such as OMPC (outer membrane protein complex) of *Neisseria meningitidis*, either by hydrophobic or covalent bonds, did not succeed in improving the quality of the antibody response against gangliosides.

Probably the characteristic of "self" antigen of GD3 was the main hinderance to an immune response with characteristics similar to T cell dependent antigens (Livingston et al (1993) Vaccine 11, 11991204).

Given the advantage of the immunogenicity of a heterophile antigen and its expression in breast tumours, N-glycolylated ganglioside based therapeutic vaccines can be effective in the treatment of human breast cancer.

Identification of a suitable antigen source is important for vaccine development. No natural source with this characteristic for N-glycolylated gangliosides has been described.

As an alternative, total synthesis of N-glycolylated ganglioside derivatives has been proposed (Ogawa et al, U.S. Pat. No. 4,950,750). This alternative has the inconvenience, as an antigen source for vaccines, that the antibodies obtained against ganglioside derivatives generally do not recognize the original gangliosides.

Nevertheless, the present invention provides a suitable natural source of antigen. GM3 and NGcGM3 are the main gangliosides in the hybridoma cells used for the industrial production of mAbs, which is an important fact for the feasibility of this therapeutic vaccine.

The use of monoclonal antibodies as protein carriers in conjugated vaccines has little precedence in general, and none in cancer therapeutic vaccines, nevertheless their use as carriers offers the advantages of immunotargeting and activation of the host's immune system.

SUMMARY OF THE INVENTION

This invention provides a vaccine composition for stimulating or increasing the immune antibody response to N-glycolylated gangliosides.

3

Thus this invention provides a vaccine composition for the prevention or treatment of cancer, containing an effective amount of a pure N-glycolylated ganglioside, mainly NGcGM3 and/or a derivative of this and/or its corresponding oligosaccharide, coupled (through hydrophobic or covalent bonds) to an appropriate vehicle and containing an adjuvant that can be for instance of natural origin or a monoclonal antibody (mAb).

The invention involves the use, as a suitable biological source of gangliosides, the hybridoma biomass used for the industrial production of monoclonal antibodies.

An aspect of the invention lies in obtaining the glycolylated gangliosides from the hybridoma biomass resulting from the industrial production of mAbs. Particularly NGcGM3, an antigen present in breast tumours can be obtained in this way. This ganglioside and/or a derivative thereof and/or its corresponding oligosaccharide is coupled to an adequate vehicle by hydrophobic binding or by covalent binding, for instance to carrier proteins, particularly mAbs.

DETAILED DESCRIPTION OF THE INVENTION:

1. OBTAINING GANGLIOSIDES FROM THE HYBRIDOMA BIOMASS.

A modification of Hakomori's method (Hakomori et al (1974), Methods in Enzymology, Vol. 32, Part B, 350) is used to process the hybridoma biomass obtained from production of mAbs in fermentors.

The biomass (0.5-1 Kg.) obtained by filtration of culture medium was homogenized with 2-5 L of methanol. Afterwards 2-5 L more were added before extraction under reflux for 5 to 20 hrs.

The extract is filtered while hot and the transparent liquid obtained left to stand 48 hours between −20° C. and −70° C.

The precipitate is recovered by centrifugation at 4° C. and submitted to medium alkaline treatment (0.2N NaOH-MeOH, 37° C. between 1 and 7 hours).

Afterwards it is neutralized with HCl-MEOH 0.2N and concentrated to dryness at a temperature below 40° C.

It is desalted by extensive dialysis at 4° C. v.s. carbonate buffer, pH 7 and then dried by lyophilization.

The monosialoganglioside fraction is obtained by ionic exchange chromatography in DEAE SEPHADEX A (Pharmacia, Sweden) Ac-form (matrix volume/sample used: 1 ml DEAE Sephadex/0.1-1 µmol of NANA), eluting with NaAc 0.02M in MeOH.

After desalting by dialysis at 4° C., the fraction is dried by lyophilization.

Purification of the gangliosides GM3 and NGcGM3 is performed by adsorption chromatography with silicagel 60 (230-400 mesh, Merck, Germany).

A column containing 10 to 40 g of silicagel, is equilibrated and eluted with $CCl_3H:MeOH:NH3$ 2.5M (v/v) 65:25:4.

The fractions that contain GM3 and NGcGM3 alone, are mixed and dried.

Column monitoring is performed by HPTLC using 10×20 cm silicagel 60 plates (Merck, Germany) with a solvent system of $CCl_3H:MeOH:NH3$ 2.5M in 0.25% KCl (50:40:10) and stained with resorcinol reagent (Svennerholm L.; Biochem. Biophys. Acta 24 (1957), 604–611).

Quantification of gangliosides is also performed by the resorcinol method. Quantities between 20-60 mg of GM3 and NGcGM3 are obtained.

2. CONSTRUCTION OF VACCINE IMMUNOGENS.

As antigens for the immunogen preparations any of the following can be used: N-glycolylated gangliosides present in the tumours; their oligosaccharides adequately modified in their reducing terminal by different spacers, that improve their access to different components of the immune system; or derivatives of these gangliosides modified by the incorporation of functional groups in the ceramide (amino, carboxyl or aldehyde groups) that allow a covalent binding to carrier proteins.

As carrier proteins any physiologically tolerated protein can be used. They should bear free amino and carboxyl groups that allow the covalent conjugation to the afore mentioned antigens using any routine conjugation method (SPDP, carbodiimides, reductive amination, etc.).

Murine monoclonal antibodies or the outer membrane proteins of different bacteria such as *Neisseria meningitidis*, can be adequate carrier proteins.

For those proteins with known primary aminoacid sequence some of the mathematical algorithms described for predicting helper T cell epitopes are used for selecting the adequate conjugation method. Thus, avoiding the possible damage of these epitopes produced by the coupling of the antigens. In this case we have used the algorithm described by Margalit et al (J. Immunol. 138, 2213–2219, 1987).

Natural gangliosides are used as components of the proteoliposomes conformed by the protein complex of the outer membrane of *N. meningitidis*. Preparation of this type of immunogen requires the previous dispersion of the proteoliposomes of *N. meningitidis* using sodium deoxycholate (0.1-1%) or dodecyl sodium sulphate (0.1-1%) or Brij 96 (0.1-1%).

Dispersion is performed in an ultrasonic bath for 10-30 minutes, adding afterwards a solution containing 5 to 20 times excess of the ganglioside (or the gangliosides should it be a multivalent vaccine). The resulting dispersion is again ultrasonicated for 5-20 minutes and is left at room temperature during 30 minutes. Finally it is dialysed until absence of detergent.

The most effective formulations of our immunogen preparations contained 2 to 5 ganglioside mass units per protein mass unit. The most effective ganglioside doses being those between 10-400 µg.

In the construction of conjugated immunogens (antigens covalently bound to carrier proteins), ganglioside oligosaccharides or structurally modified gangliosides can be used.

When ganglioside oligosaccharides are used as antigens a spacer arm must be added to increase distance, avoiding crypticity and making them more available to the immune system.

As spacer reagents aliphatic compounds (3 to 10 carbon atoms) that contain one free amino group in one end and a carboxyl group or an amino group in the other end of the chain can be used.

The coupling of the saccharide to the spacer reagent is performed by a reductive amination reaction (Stoll M. S. et al, Biochem. J. 256, 661–664, 1988), using sodium cyanoborohydride as a reductive agent.

Typical reaction conditions are: oligosaccharide (5-25 µmol), spacer arm (250-1250 µmol), sodium cyanoborohydride (5-25 mg), reaction temperature (40°-70° C.) and reaction time (24-72 hours).

The aminated oligosaccharide thus obtained is then coupled to N-succinimidyl 3-(2-pyridyldithio)propionate (SPDP, Carlsson J., Biochem. J. 173, 723–737, 1978), at 3–5 times molar excess relative to the oligosaccharide, at room temperature for 6-10 hours.

Next it is necessary to couple the carrier protein to the SPDP using a 3–5 molar excess relative to the oligosaccharide in a reaction at room temperature for 4–12 hours.

The reduction of the SPDP-protein complex was performed by a 10–50 mM dithiothreitol solution at room temperature for 1–5 hours. Finally coupling between the aminated oligosaccharide-SPDP and the reduced protein-SPDP complex is performed in a reaction in which the sugar is used in a 2–5 molar excess relative to the number of free amino groups in the proteins. The reaction occurs at room temperature between 24–72 hours.

Under these conditions 10–100 moles of the oligosaccharide (or its equivalent in mass) are coupled to the carrier proteins.

Another way of constructing immunogens to be used in multivalent vaccines involve the two methods previously described: the formation of proteoliposomes in which one or more gangliosides are bound noncovalently and the covalent bond of one oligosaccharide from a ganglioside to which a spacer arm has been coupled.

The following examples are illustrative:

EXAMPLE 1

Isolation of GM3 and NGcGM3 from the hybridoma biomass.

The hybridoma biomass obtained from production in fermentors of monoclonal antibody ior t3 (CIMAB S.A., Cuba) was processed using a modification of Hakomori's method (Hakomori et al., (1974), Methods in Enzymology, Vol.32 Part B, 350).

The hybridoma biomass (500 g) obtained by filtration of the culture medium, was homogenized with methanol (2.5 L) using a homogenizer. More methanol was added (2.5 L) and extraction under reflux during ten hours was performed. The extract was filtered while hot and the transparent liquid obtained left to rest at −20° C. during 2 days.

The precipitate was recovered by centrifugation at 4° C. and submitted to medium alkaline treatment (0.2N NaOH/MeOH, 37° C., 2 h). After neutralizing with HCl 0.2N, it was dried in a roto-evaporator and the solid was desalted by extensive dialysis at 4° C. against carbonate buffer pH 7. The dialysed product was freeze dried.

The monosialoganglioside fraction was obtained by ionic exchange chromatography in DEAE SEPHADEX A-25 (Ac) eluting with NaAc 0.02M in MeOH. After desalting by dialysis this fraction was lyophilized, dissolved in $CCl_3H$:MeOH:$NH_3$ 2.5M (65:24:4) and applied to a 35 grams silicagel 60 column.

The column was eluted with a mixture of $CCl_3H$:MeOH:$NH_3$ 2.5M (65:25:4) obtaining the corresponding gangliosidic fractions.

The fractions containing GM3 and NGcGM3 alone were mixed and dried using a roto-evaporator.

The determination of ganglioside contents in the different fractions of the silicagel separation was performed by high performance thin layer chromatography (HPTLC) in silicagel 60 plates with $CCl_3H$/MeOH/NH3 2.5M in KCl 0.25% (50:40:10) solvent system and stained with resorcinol.

Yields of 30 mg of GM3 and 24 mg of NGcGM3 were obtained.

EXAMPLE 2

Obtaining an immunogen based on non covalent coupling of the ganglioside NGcGM3 to the outer membrane protein complex (OMPC) of *N. meningitidis*.

The OMPC of *N. meningitidis* provided by "Carlos J. Finlay" Institute (C. Campa et al European Patent application 301992) were used.

10 mg of the OMPC were dispersed for 10 minutes in a 0.3% solution of sodium deoxycholate in an ultrasonic bath. Then, a solution containing 20 mg of NGcGM3 ganglioside was added. The resulting dispersion was again submitted to ultrasonic radiation during 5 minutes, leaving it to rest afterwards for 30 minutes.

The separation of the soluble complex OMPC-NGcGM3 from the detergent was performed by dialysis, during 5 days using a 100 kD membrane.

The grade of incorporation of the ganglioside to the protein was determined using the Bio-Rad reagent for the proteins and resorcinol for the sialic acid.

An incorporation of 2 mg of NGcGM3 per mg of OMPC was obtained.

EXAMPLE 3

Obtaining the immunogen (neoglycoproteins) based on the covalent binding of the oligosaccharide component of the NGcGM3 ganglioside to the P3 murine mAb.

a) Isolation of the oligosaccharide component of NGcGM3 (NGcGM3OS).

10 mg of NGcGM3 were dissolved in 4 ml of MeOH with the aid of an ultrasonicator and treated with ozone (Wiegandt H. and Baschang G. Z. Naturforsch., 20b:164–166, 1965) during 10 minutes.

The solution was evaporated to dryness and the residue dispersed in 10 ml of $Na_2CO_3$ 0.1M by stirring overnight, neutralized with DOWEX 50W-X8 and filtered through a sintered glass funnel.

The resulting solution was extracted with $HCCL_3$ and the aqueous phase was studied by HPTLC to determine the completion of the reaction.

The presence of oligosaccharide was verified by a positive resorcinol stain in the application point.

The final purification of NGcGM3OS was performed in a SEPHADEX G-25 column using HAc 0.1M for elution.

The structure of NGcGM3OS was finally determined by H1 Nuclear Magnetic Resonance and mass spectrometry (FAB spectrum).

b) Reductive amination of $NGcGM_3OS$.

10 µmol of NGcGM3OS were dissolved in 5 ml of methanol containing 500 µmol of 1–8 diamine-3,6-dioxooctane, purged with argon and left to react during 2 hours at 50° C. after which 10 mg of $NaBH_3CN$ were added and the reaction continued for 40 hours at 50° C.

The reaction mixture was dried under argon and AcH added to eliminate the excess of NaBH3CN.

The modified oligosaccharide was desalted in a Biogel P-2 column and purified in a CM-cellulose column (Zopf et.al., Methods Enzymol.50:171–175, 1978).

The identification of the aminated derivative was performed by HPTLC using silicagel 60 plates in pyridine-ethyl acetate-acetic acid-water (6:3:1:3) or chloroform-methanol-0.2% calcium chloride (60:35:8) solvents and detected with orcinol or resorcinol reagents.

c) Reaction of the aminated NGcGM3OS with the coupling reagent N-succinimidyl 3- (2-pyridyldithio) propionate (SPDP).

10 µmol of the oligosaccharide were dissolved in phosphate buffer solution 100 mM, NaCl 0 .1M, pH 7.5, then 30–50 µmol of SPDP was added and left to react during 6 hours at room temperature. The derivative obtained was purified using a Biogel P2 column.

The identification of the derivative obtained was performed by HPTLC using the same plates, solvents and detection systems as in step b.

d) Reaction of the monoclonal antibody P3 with SPDP.

10 mg of the P3 monoclonal antibody, an IgM mAb that recognizes with high specificity N-glycolyl neuraminic acid bound to lipids, was dissolved at room temperature in phosphate buffer solution 100 nM, NaCl 0.1M, pH 7.5. A cell line producing P3 was deposited with the Centre for Applied Microbiology and Research Microbiological Research Authority (European Collection of Animal Cell Cultures), Porton Down, in accordance with the Budapest Treaty, on Nov. 30, 1994 as Deposit ref. 94113026. To this solution was added 5 mg of SPDP and the reaction left to continue for 8 hours. The separation of P3-SPDP was performed in a SEPHADEX G-50 column using for elution a phosphate buffer solution 0.1M, pH 6, 5 mM EDTA.

The fractions containing the protein were mixed and used for the following step.

e) Reduction of P3-SPDP derivative with dithiothreitol.

To reduce the new generated disulphide bridges a 25 mM dithiothreitol solution in phosphate buffer solution 0.1M, pH 6, 5 mM EDTA was added and allowed to react at room temperature during 2 hours.

The derivative obtained was separated in a SEPHADEX G-50 column using for elution the same solution referred above.

The calculation of the number of SPDP moles coupled to P3 was estimated by calculating the free thiopyridine formed during the coupling process and is based on the measuring in an spectrophotometer of the extinction increase at the wavelength of 343 nm and the application of the Lambert-Beer law. A molar extinction coefficient for thiopyridine of $7.06 \times 10-9 \times M-1 \times cm-1$. was used.

f) Carbohydrate coupling to protein.

The carbohydrate derivative obtained in step c was allowed to react during 48 hours with the protein obtained in step e.

The neoglycoprotein obtained was separated from the reaction products using a SEPHADEX G-50 column.

The estimation of the amount of carbohydrate coupled to the protein was determined by calculating the sialic acid content using the resorcinol reagent for the carbohydrate and Bio-Rad reagent for the protein.

25 moles of NGcGM3OS per mol of P3 were obtained in these conditions.

The carbohydrate coupling to protein was also studied by electrophoresis in polyacrylamide gel (SDS-PAGE) under non reducing conditions followed by Western blot and reaction with anti-ganglioside specific mAbs.

EXAMPLE 4

Obtaining the immunogen (Neoglycoproteins) by using the OMPC of the *N. meningitidis*, previously solubilized with the ganglioside NGcGM3 and then covalently coupled to NGcGM3OS.

a) Solubilization of the OMPC.

Solubilization of the OMPC was performed according to Example 2.

b) Coupling of NGcGM3OS to the OMPC-NGcGM3 soluble complex.

The oligosaccharide NGcGM3OS was obtained as described in step a of Example 3, submitted to reductive amination as in step b of Example 3 and coupled to SPDP as described in step c of Example 3.

In parallel the soluble protein complex OMPC-NGcGM3 was coupled to the SPDP reagent as described in step d of Example 3, reduced with dithiothreitol as described in step e of Example 3 and finally coupled to the appropriate carbohydrate as described in step f of Example 3.

In all cases the amount of reagents and reaction conditions were those specified in Example 3.

The analytical methods used for the characterization of the different NGcGM3 derivatives as well as those used for the characterization of the OMPC and its derivatives were the same as those described in Example 3.

An incorporation degree of 1 mg of NGcGM3OS per mg of OMPC proteoliposomes was obtained.

EXAMPLE 5

Immunological properties of the vaccine composition. Immunization of chickens.

The different variants of the vaccine composition described above were used to immunize chickens and study the specific humoral immune responses obtained.

As reference a group of chickens immunized weekly during one month with 1 mg NGcGM3 in 0.6 ml of PBS using Freund's complete adjuvant were used.

Two weeks after the 4th doses a booster was applied and four days later the animals were bled.

The same immunization protocol was used for the groups of chickens treated with each vaccine preparation.

The antibody response was evaluated by ELISA and TLC immuno-staining, using the ganglioside NGcGM3 as antigen.

In all the groups of chickens immunized with the vaccine preparations, an increase in the levels of specific antibodies against NGcGM3 ganglioside with respect to the pre immune serum was obtained.

The control group also showed an increase in antibody response but of the IgM type, while all the vaccine preparations consistently showed a specific IgG response in most of the animals immunized.

EXAMPLE 6

Gangliosides expressed in breast tumours.

Biopsies of ten breast tumours were obtained during surgery. Samples were histologically classified and stored at −70° C. until use.

Tumors were processed individually following the method briefly described below:

To wet and weighed tumors were added 3 volumes of distilled water and homogenized in the cold (4° C).

Total protein contents was determined in a sample of the homogenate by the Lowry method. To the remaining volume of each sample was added 5 volumes of a mixture of $CCl_3H$-$CH_3OH$ (2:1) and stirred during 1 hour at 37° C. Then $CH3OH$ was added to adjust the ratio of $CCl_3H:CH_3OH$ to 1:1 and the extraction procedure repeated. The final mixture was centrifuged, separating the supernatant.

Precipitate was again extracted by stirring at 37° C. during 2 hours with a mixture of $CCl_3H:CH_3OH:H_2O$ (1:2:0.8). It was again centrifuged separating supernatant.

Both supernatants were mixed and concentrated to dryness obtaining the mixture of total lipids of each tumour.

The mixtures of total lipids dissolved in 5 ml of $CCl_3H:CH_3OH$ (9:1) were applied to Phenyl Sepharose columns (2 ml) and washed with 3 volumes of the same solvent mixture followed by $CCl_3H:CH_3OH$ (85:15).

Gangliosides were eluted afterwards with 5 volumes of $CCl_3H:CH_3OH$ (1:1) and 5 volumes of $CH_3OH$.

The individual samples of the tumour ganglioside mixtures were studied by HPTLC and 2d-HPTLC by the method of Sonnino et.al.(Anal. Biochem. 128 (1983) 104–114). The relative amounts of the main gangliosides were estimated by densitometry.

The results obtained indicate that the main gangliosides in breast tumours are $GM_3$ (average: 356.4 ng/mg protein) and $GD_3$ (average: 133.1 ng/mg protein) followed by $GD_{1a}$ and $GT_{1b}$.

The expression of GM3 and GD3 in normal breast tissue is as average (183.5 and 48.6 ng/mg protein respectively) lower than in breast tumours.

For the characterization of the minor breast tumour gangliosides a pool with a mass of 83 grams was also studied.

This tumour mass was processed and extracted as previously described.

The total mixture of gangliosides was submitted to ionic exchange chromatography in DEAE Toyopearl and the total acid fraction submitted again to chromatography in a Q-Sepharose column with a gradient system from which 9 fractions were obtained. The chromatographic studies in 2d-HPTLC combined with FAB-MS and the TLC immunostaining experiments with a monoclonal antibody specific to O-acetylated gangliosides allowed the detection of the presence of $OAcGD_3$ and $OAcGT_3$ in the sample studied.

It was also possible to detect in the ganglioside mixtures of breast tumours the presence of bands with an identical Rf as NGcGM3. The TLC immunostaining study with antibodies that react with H-D antigens showed, additionally, the presence of 2 other glycolylated gangliosides.

TLC immunostaining studies were performed both with H-D and the anti-OAc ganglioside mAbs for the mixture of gangliosides obtained from 10 individual tumours. Results are shown in Table I.

After eliminating the excess of acetic anhydride by evaporation with MeOH, the samples were dissolved in $CCl_3H$ and were submitted to GC/MS in a Jeol DX-304 equipment with an OV-17 column (0.25 mm×5 m) using the electronic impact mode.

The temperature of the column was 228° C. and of the injector was 260° C. The carrier gas used was He at 0.5 ml/min. Results are shown in Table II.

TABLE II

Analysis of Sialic acid Species (Composition)

| Sample No.[a] | | NANA[b] | NGNA[b] | O—Ac NANA[b] |
|---|---|---|---|---|
| 3849 | GC/MS | 75.11%[c] | 16.60% | 8.20% |
| 3464 | GC/MS | 89.20% | 5.82% | 4.89% |
| 3931 | GC/MS | 76.55% | 11.55% | 11.89% |
| 3806 | GC/MS | 88.56% | | 11.44% |

NOTES:

[a]3849, 3464, 3931, 3806, are individual tumour samples (see table I),

[b]NANA: N acetyl Neuraminic acid NGNA: N glycolyl Neuraminic acid, O Ac NANA: O Acetyl N Acetyl Neuraminic Acid,

[c]Values are percent of total lipid bound sialic acid.

TABLE I

Presence of H-D antigens in the total ganglioside fraction isolated from human breast tumuors

| | | SAMPLE | | | | | | | | | |
|---|---|---|---|---|---|---|---|---|---|---|---|
| | METHOD | 3705[b] | 3735 | 3782 | 3820 | 3931 | 3464 | 3806 | 3849 | 3523 | 3734 |
| GM3 (NGNA) [c] | Immuno-staining (a) | + | + | + | + | ++++ | + | − | +++ | − | + |
| U1 (NGNA) (d) | Immuno-staining (a) | − | + | ++ | − | ++ | ++ | − | ++ | − | ++ |
| U2 (NGNA) (d) | Immuno-staining (a) | − | − | − | − | + | − | − | − | − | − |

NOTES:

(a) TLC-immunostaining with H-D antibody.

(b) 3705, 3735, 3782, etc, are individual human breast tumuor samples (c) NGNA: N Glycolyl Neuraminic acid (N-glycolyl)

(d) U1 and U2: unknown N Glycolylated gangliosides (N glycolylated)

(e) +, low reactivity; +++, middle reactivity; ++++, high reactivity; −, no reactivity.

The relative amounts of the different types of lipidbound sialic acids in breast cancer were studied in 4 tumors.

For this purpose the mixtures of individual gangliosides were submitted to methanolysis in 0.5% HCl/MeOH at 100° C. for 2 hours.

Samples were dried under N2 atmosphere and 0.5 μg of phenyl-α-N-acetylglucosaminide was added as an internal standard. Samples were then acetylated in a mixture of acetic anhydride:pyridine (1:1) at 100° C. for 30 minutes.

We claim:

1. A vaccine composition for stimulating or increasing the antibody immune response against N-glycolylated gangliosides comprising N-glycolyl GM3 (NGcGM3) coupled to a carrier protein and an adjuvant.

2. The vaccine composition of claim 1 wherein the NGcGM3 is present in said vaccine composition in an amount between 10 and 400 μg.

3. The vaccine composition of claim 1 wherein the carrier protein comprises the outer membrane protein complex (OMPC) of *Neisseria meningitidis*.

4. The vaccine composition of claim 3 wherein the immunogen comprises a soluble complex of NgcGM3 and the OMPC of N. meningitidis and wherein said immunogen is coupled by a covalent bond to the N-glycolylated ganglioside oligosaccharide through a spacer arm.

5. The vaccine composition of claim 1 wherein the carrier protein is a monoclonal antibody.

6. The vaccine composition of claim 5 wherein the monoclonal antibody is coupled by a covalent bond to NGcGM3 using a spacer arm.

7. The vaccine composition of claim 4 wherein the spacer arm is a saturated or unsaturated diamine containing 3–10 carbon atoms.

8. The vaccine composition of claim 1 wherein the vaccine composition further comprises an immunogen selected from the group of immunogens consisting of the purified GM3 ganglioside and the corresponding oligosaccharide.

9. The vaccine composition of claim 1 wherein the vaccine composition further comprises an immunogen selected from the group of immunogens consisting of the purified GD3 ganglioside and the corresponding oligosaccharide.

10. The vaccine composition of claim 8 wherein the GM3 ganglioside is purified from a biological source.

11. The vaccine composition of claim 10 wherein the biological source is a hybridoma biomass used in the production of a monoclonal antibody.

12. The vaccine composition of claim 1 wherein the NGcGM3 is purified from a biological source.

13. The vaccine composition of claim 12 wherein the biological source is a hybridoma biomass used in the production of monoclonal antibodies.

14. A method of stimulating or increasing the immune response in an animal comprising administering a vaccine composition according to claim 1 to the animal.

15. A method of obtaining an immune response in an animal comprising immunizing said animal with the vaccine composition of claim 1.

16. A method according to claim 15 wherein the vaccine composition further comprises an immunogen selected from the group of immunogens consisting of the purified GM3 ganglioside and the corresponding oligosaccharide.

17. A method according to claim 15 wherein the vaccine composition further comprises an immunogen selected from the group of immunogens consisting of the purified GD3 ganglioside and the corresponding oligosaccharide.

18. The method of claim 15 wherein between 10 and 400 µg of the NGcGM3 is administered per dosage unit.

* * * * *